United States Patent
Mori et al.

(10) Patent No.: US 9,512,385 B2
(45) Date of Patent: Dec. 6, 2016

(54) DISINFECTANT SOLUTION FOR NONIONIC SOFT CONTACT LENSES

(71) Applicant: MENICON CO., LTD., Nagoya-shi, Aichi (JP)

(72) Inventors: Osamu Mori, Kasugai (JP); Megumi Toyohara, Kasugai (JP); Yuri Matsui, Kasugai (JP)

(73) Assignee: MENICON CO., LTD., Aichi (JP)

( * ) Notice: Subject to any disclaimer, the term of this patent is extended or adjusted under 35 U.S.C. 154(b) by 0 days.

(21) Appl. No.: 14/719,715

(22) Filed: May 22, 2015

(65) Prior Publication Data
US 2015/0252297 A1    Sep. 10, 2015

Related U.S. Application Data

(63) Continuation of application No. PCT/JP2012/082150, filed on Dec. 12, 2012.

(51) Int. Cl.
| | |
|---|---|
| *A01N 37/46* | (2006.01) |
| *A01N 25/02* | (2006.01) |
| *A01N 33/12* | (2006.01) |
| *A61L 12/14* | (2006.01) |
| *C11D 3/00* | (2006.01) |
| *C11D 3/33* | (2006.01) |
| *C11D 3/48* | (2006.01) |

(52) U.S. Cl.
CPC ............ *C11D 3/0078* (2013.01); *A01N 37/46* (2013.01); *C11D 3/33* (2013.01); *C11D 3/48* (2013.01); *A61L 12/14* (2013.01); *A61L 12/142* (2013.01); *A61L 12/145* (2013.01)

(58) Field of Classification Search
None
See application file for complete search history.

(56) References Cited

U.S. PATENT DOCUMENTS

| 6,187,264 B1 | 2/2001 | Osawa et al. |
|---|---|---|
| 2005/0074467 A1 | 4/2005 | Fujita et al. |
| 2006/0122080 A1* | 6/2006 | Mori ............... A01N 33/12 |
| | | 510/112 |
| 2010/0240561 A1 | 9/2010 | Lee et al. |

FOREIGN PATENT DOCUMENTS

| EP | 2 666 484 A1 | 11/2013 |
|---|---|---|
| JP | 2000-084052 A | 3/2000 |
| JP | 2000084052 A * | 3/2000 |
| JP | 2001-264707 A | 9/2001 |
| JP | 2002-143277 A | 5/2002 |
| JP | 2006-201247 A | 8/2006 |
| JP | 3894945 B2 | 3/2007 |
| JP | 4255839 B2 | 4/2009 |
| JP | 2009-175543 A | 8/2009 |
| WO | 94/13774 A1 | 6/1994 |
| WO | 97/27879 A1 | 8/1997 |
| WO | 03/067311 A1 | 8/2003 |
| WO | 2012/098653 A1 | 7/2012 |

OTHER PUBLICATIONS

Good, Jr., et al. "Colorimetric Determination of a Polymeric Quaternary Ammonium Antimicrobial Preservative in an Ophthalmic Solution," J. Assoc. Off. Anal. Chem., 1987, vol. 70, No. 6, pp. 979-980.
Feb. 12, 2013 International Search Report issued in International Application No. PCT/JP2012/082150.

* cited by examiner

*Primary Examiner* — Gigi Huang
(74) *Attorney, Agent, or Firm* — Oliff PLC

(57) ABSTRACT

A disinfecting solution for a nonionic soft contact lens, which solution contains polylysine as a disinfectant, and further contains: 0.1-1.0% by weight of a component (A) which is an acidic tonicity agent having at least one carboxyl group; 0.10-1.25% by weight of a component (B) which is a basic tonicity agent having an amino group; and 0.1-2.0% by weight of a component (C) which is at least one of a nonionic tonicity agent and an amphoteric tonicity agent, wherein each of the components (A) to (C) has a molecular weight of not larger than 200, and a ratio of a molar concentration of the component (A) to a molar concentration of the component (B) is not larger than 1.2. The disinfecting solution has a pH of 6.5-8.0, an osmotic pressure of 250-330 mOsm/kg and an electric conductivity of 130-750 mS/m.

17 Claims, No Drawings

DISINFECTANT SOLUTION FOR NONIONIC SOFT CONTACT LENSES

CROSS REFERENCE TO RELATED APPLICATION

This application is a continuation of the International Application No. PCT/JP2012/082150 filed on Dec. 12, 2012, the entireties of which are incorporated herein by reference.

BACKGROUND OF THE INVENTION

1. Field of the Invention

The present invention relates to a disinfecting solution for a nonionic soft contact lens, and particularly relates to a disinfecting solution for a nonionic soft contact lens which solution contains at least polylysine as a disinfectant.

2. Description of Related Art

A disinfecting solution for a soft contact lens has been prepared by using polyhexamethylene biguanide (PHMB) and polyquaterniums as disinfectants for the soft contact lens. PHMB has a biguanide group as a repeating unit of its main chain, and the polyquaterniums have a quaternary ammonium group as a repeating unit of their main chains. The biguanide group and the quaternary ammonium group have positive charges in an aqueous solution, so that PHMB and the polyquaterniums electrostatically adsorb to negatively charged phospholipids existing in cell membranes of microorganisms, thereby exhibiting disinfecting effects. Although the disinfecting effects of PHMB and the polyquaterniums are powerful, these disinfectants exhibit high degrees of cytotoxicity, so that the use of PHMB and the polyquaterniums at an extremely high concentration should be avoided. On the other hand, even where those disinfectants are used at a relatively low concentration, the disinfectants tend to accumulate on a surface of the contact lens subjected to a hydrophilic treatment, which surface is negatively charged, giving rise to a problem of toxicity of the accumulated disinfectants. Under the above-described circumstances, efforts have been made to develop a disinfectant which exhibits a high degree of disinfecting effect and a low degree of cumulative toxicity with respect to the soft contact lens. Also, studies have been made to provide a disinfectant configured to reduce the cumulative toxicity with respect to the soft contact lens. However, such disinfectants have not been obtained yet.

On the other hand, polylysine used for disinfecting the contact lens is known as a polymer disinfectant, like the above-described PHMB and polyquaterniums. Polylysine has a lysine which is an amino acid, as a repeating unit, and considered to exhibit the disinfecting effect by electrostatic adsorption to surfaces of the microorganisms via a primary amine group. Further, polylysine has an extremely low degree of toxicity, since it has the lysine which is the amino acid, as the repeating unit. The extremely low degree of toxicity of polylysine is proved by a cytotoxicity test in which the $IC_{50}$ value of polylysine is confirmed to be about several hundredth part of that of PHMB, for example. Accordingly, in the case where polylysine is used, a risk of eye disorders is evidently lower than in the case where PHMB is used, assuming that substantially the same amount of polylysine and PHMB accumulate on the contact lens.

However, it was revealed that where a component having a high degree of ionic strength is contained in the aqueous solution together with polylysine, the electrostatic adsorption of polylysine to the surfaces of the microorganisms is hindered, resulting in deterioration of the disinfecting effect, since the primary amine group of polylysine, which group is the active site of disinfection, has a weaker positive charge in the aqueous solution, than the biguanide group of PHMB and the quaternary ammonium group of the polyquaterniums.

Moreover, the electrostatic adsorption of the disinfectant is hindered by additives such as a surfactant, a buffer, a tonicity agent and a chelating agent, which are generally contained in the disinfecting solution for the soft contact lens, together with a disinfecting component (the disinfectant). Particularly, the tonicity agent is contained at a high concentration in the disinfecting solution for the soft contact lens, so that where an inorganic tonicity agent such as NaCl having a high degree of ionic strength (electric conductivity) exists in the disinfecting solution, together with polylysine, the disinfecting effect of polylysine is considerably deteriorated. Thus, where polylysine is used as the disinfectant, problems may be caused by the additives which do not cause problems when they are used together with the conventionally used disinfectants such as PHMB and the polyquaterniums.

For the reasons described above, in order for the disinfecting solution using polylysine having the low degree of toxicity to exhibit a sufficiently high disinfecting effect, precise reconsideration of the composition of the disinfecting solution is required.

By the way, JP-A-2000-84052 proposes to use, as the disinfecting solution, a contact lens solution containing the amino acid and/or a nonionic tonicity agent together with ε-polylysine used as a sterilizing component. This publication discloses examples of the contact lens solution containing components which increase the ionic strength, such as sodium phosphate, sodium glutamate and sodium chloride, and examples of the contact lens solution in which the nonionic tonicity agent such as propylene glycol is used in combination with a boric acid. JP-A-2006-201247 proposes a contact lens disinfecting and preserving solution containing an organic cationic compound and a lactic acid together with ε-polylysine, and a contact lens disinfecting and preserving solution further containing inositol or glycerol together with the organic cationic compound, the lactic acid and ε-polylysine. This publication discloses examples of the contact lens disinfecting and preserving solution containing the boric acid used as a pH buffer together with the above-indicated components.

However, in the case where an osmotic pressure of the disinfecting solution is adjusted by using the nonionic tonicity agent in the form of a low-molecular-weight polyhydric alcohol, a neutral amino acid and the like, which are disclosed in the above-indicated publications, swelling of a nonionic soft contact lens is likely to be caused by the nonionic tonicity agent. Accordingly, where tonicity is adjusted by increasing the osmotic pressure of the disinfecting solution to about 290 mOsm/kg by using the nonionic tonicity agent only, the nonionic soft contact lens considerably swells such that its dimensions exceed prescribed limits. On the other hand, in the case where auxiliary disinfecting components having an antiseptic effect, such as the boric acid and the lactic acid, are used together with polylysine, for the purpose of supplementing the disinfecting effect of polylysine to improve the disinfecting effect of the disinfecting solution, the use of the boric acid gives rise to problems of an increase of cytotoxicity of the disinfecting solution and a dimensional change of the nonionic soft contact lens, while the use of the lactic acid gives rise to an inherent problem that the lactic acid in the form of crystals is deposited on the surface of the nonionic soft contact lens, as pointed out in Japanese Patent No. 3894945.

On the other hand, in order to further improve the disinfecting effect of the disinfecting solution, proposals have been made regarding use of a second disinfectant in combination with polylysine used as a first disinfectant. For example, Japanese Patent No. 4255839 proposes a contact lens solution containing polylysine, a polyphosphoric acid (salt) and a nitrogen-containing organic antimicrobial agent (such as PHMB and the polyquaterniums). However, the use of the polyphosphoric acid (salt) is effective to prevent polylysine from adsorbing to the contact lens, but gives rise to a problem of deterioration of the disinfecting effect of polylysine. Further, the nitrogen-containing organic antimicrobial agents such as PHMB and the polyquaterniums, which have more powerful disinfecting effects than polylysine, cannot be effectively prevented from adsorbing to the contact lens, so that the disinfecting solution cannot sufficiently exhibit the disinfecting effect, and there arises a problem of cytotoxicity due to the disinfectants adsorbing to the contact lens and accumulated thereon.

SUMMARY OF THE INVENTION

The present invention was made in view of the background art described above. It is therefore an object of the present invention to provide a disinfecting solution for a nonionic soft contact lens, which solution contains polylysine as the disinfectant and exhibits an excellent disinfecting effect. It is another object of the present invention to provide a disinfecting solution which can advantageously assure the disinfecting effect of polylysine without using auxiliary disinfectants such as the boric acid and the lactic acid, and additives such as sodium chloride and the polyphosphoric acid (salt), which deteriorate the disinfecting effect of polylysine, while effectively reducing or preventing the dimensional change of the contact lens, to have improved compatibility with respect to the nonionic contact lens.

To achieve the above-described objects, the present invention can be embodied in various preferred modes which will be described below. The preferred modes of the invention described below may be practiced in any combination. It is to be understood that the preferred modes and technical features of the present invention are not limited to those described below, and can be recognized based on the inventive concept disclosed in the whole specification.

(1) A disinfecting solution for a nonionic soft contact lens, which solution contains polylysine as a disinfectant, characterized in that: the disinfecting solution further contains 0.1-1.0% by weight of a component (A) which is an acidic tonicity agent having at least one carboxyl group and a molecular weight of not larger than 200, 0.10-1.25% by weight of a component (B) which is a basic tonicity agent having an amino group and a molecular weight of not larger than 200, and 0.1-2.0% by weight of a component (C) which is at least one of a nonionic tonicity agent and an amphoteric tonicity agent each of which has a molecular weight of not larger than 200, wherein a ratio ($\alpha/\beta$) of a molar concentration ($\alpha$) of the above-described component (A) to a molar concentration ($\beta$) of the above-described component (B) is not larger than 1.2; and the disinfecting solution has a pH of 6.5-8.0, an osmotic pressure of 250-330 mOsm/kg and an electric conductivity of 130-750 mS/m.

(2) The disinfecting solution for the nonionic soft contact lens according to the above-described mode (1), further containing a second disinfectant having at least two repeating units of a biguanide group or a quarternary ammonium group in its main chain, in addition to a first disinfectant consisting of the above-described polylysine.

(3) The disinfecting solution for the nonionic soft contact lens according to the above-described mode (1) or (2), wherein the acidic tonicity agent is selected from a group consisting of a glycolic acid, a tartaric acid, a malic acid, a fumaric acid, a maleic acid, an aspartic acid, a glutamic acid and a citric acid.

(4) The disinfecting solution for the nonionic soft contact lens according to any one of the above-described modes (1) to (3), wherein the basic tonicity agent is selected from a group consisting of ammonia, monoethanolamine, diethanolamine, triethanolamine, 2-amino-2-methyl-1-propanol, 2-amino-2-methyl-1,3-propanediol, and trometamol.

(5) The disinfecting solution for the nonionic soft contact lens according to any one of the above-described modes (1) to (4), wherein the nonionic tonicity agent is selected from a group consisting of propylene glycol, glycerol, 1,3-propanediol, butylene glycol, erythritol, sorbitol, mannitol and xylitol.

(6) The disinfecting solution for the nonionic soft contact lens according to any one of the above-described modes (1) to (5), wherein the amphoteric tonicity agent is selected from a group consisting of glycine, trimethylglycine, taurine and serine.

(7) The disinfecting solution for the nonionic soft contact lens according to any one of the above-described modes (1) to (6), wherein the above-described polylysine is $\epsilon$-polylysine.

(8) The disinfecting solution for the nonionic soft contact lens according to the above-described mode (2), wherein the above-described second disinfectant is selected from a group consisting of polyhexamethylene biguanide, alexidine, polyquaternium-1 and polyquaternium-6.

(9) The disinfecting solution for the nonionic soft contact lens according to any one of the above-described modes (1) to (8), wherein the above-described ratio ($\alpha/\beta$) is not larger than 1.0.

(10) The disinfecting solution for the nonionic soft contact lens according to any one of the above-described modes (1) to (9), wherein a concentration of the above-described polylysine is 1-1000 ppm.

(11) The disinfecting solution for the nonionic soft contact lens according to any one of the above-described modes (1) to (10), wherein a concentration of the above-described polylysine is 10-500 ppm.

(12) The disinfecting solution for the nonionic soft contact lens according to the above-described mode (2), wherein a concentration of the above-described second disinfectant is 0.1-50 ppm.

(13) The disinfecting solution for the nonionic soft contact lens according to the above-described mode (2), wherein a concentration of the above-described second disinfectant is 0.5-20 ppm.

In the present invention, the disinfecting solution is composed without using the conventionally used auxiliary disinfectants such as the boric acid and the lactic acid, which would cause problems, and the tonicity agent and the additives such as sodium chloride and the polyphosphoric acid (salt), which would cause deterioration of the disinfecting effect of polylysine. The disinfecting solution according to the present invention is composed so as to contain the combination of the three kinds of specific low-molecular-weight tonicity agents used at the respective predetermined concentrations, and such that the electric conductivity of the disinfecting solution as a whole is adjusted within the adequate range. Therefore, the disinfecting solution for the nonionic soft contact lens according to the present invention can advantageously exhibit the disinfecting effect of polylysine and excellent compatibility with respect to the contact lens, while effectively mitigating cytotoxicity of the disinfectant.

Further, it was found that in the disinfecting solution according to the present invention, which solution contains the three kinds of tonicity agents in a well-balanced manner, and whose electric conductivity is adjusted within the adequate range, even where the disinfecting solution further contains, in addition to polylysine used as the first disinfectant, the second disinfectant such as PHMB and the polyquaterniums, which have at least two repeating units of the biguanide group or the quarternary ammonium group in their main chains, adsorption and accumulation of the second disinfectant on the contact lens can be advantageously reduced or prevented, while the disinfecting solution maintains the above-described excellent compatibility with respect to the contact lens. Therefore, a further improvement of the disinfecting effect can be achieved by the use of the first and second disinfectants. Also, even where the disinfecting solution contains the second disinfectant having a relatively strong positive charge in the aqueous solution, the problem of cytotoxicity due to accumulation of the second disinfectant on the contact lens can be advantageously prevented.

DETAILED DESCRIPTION OF THE INVENTION

Polylysine which is used as a (first) disinfectant in a disinfecting solution for a nonionic soft contact lens according to the present invention is a polymer of L-lysine, and generally has about 20 to 50 lysine-bond residues (or lysine units), as is well known in the art. Polylysine is obtained from L-lysine by a generally employed organic synthesis process, for example, or can be industrially produced by culturing microorganisms belonging to genus *Streptomyces* by utilizing a biotechnological technique. Polylysine is classified into α-polylysine in which an amino group at an α-position is condensed with a carboxyl group at the α-position, and ε-polylysine in which the amino group at an ε-position is condensed with the carboxyl group at the α-position. Among these two kinds of polylysine, ε-polylysine is preferably used in the present invention.

In the present invention, polylysine is contained in the disinfecting solution in an amount sufficient to achieve the desired disinfecting effect, but generally contained at a low concentration of not higher than 1000 ppm, and preferably not higher than 500 ppm, since an excessively large amount of polylysine gives rise to a risk of an increase of an amount of polylysine adsorbing to the contact lens and accumulated thereon. In order for the disinfecting solution to sufficiently exhibit the desired disinfecting effect, polylysine is generally contained in the disinfecting solution at a concentration of not lower than 1 ppm, and preferably not lower than 10 ppm.

In the present invention, three kinds of low-molecular-weight tonicity agents are used in combination with polylysine used as the disinfectant, in order to improve compatibility of the disinfecting solution with respect to the nonionic soft contact lens, and to enable the disinfecting solution to advantageously exhibit the disinfecting effect of polylysine in the absence of conventionally used auxiliary disinfectants such as a boric acid and a lactic acid, which would cause problems. The three kinds of low-molecular-weight tonicity agents are: (A) an acidic tonicity agent having at least one carboxyl group; (B) a basic tonicity agent having an amino group; and (C) at least one of a nonionic tonicity agent and an amphoteric tonicity agent. Each of these tonicity agents has a molecular weight of not larger than 200. Where only one or two of the above-indicated three kinds of low-molecular-weight tonicity agents is/are used, there arises at least one problem in properties of the disinfecting solution, such as the disinfecting effect and compatibility with respect to the contact lens, so that it is difficult to sufficiently achieve the objects of the present invention. Further, where the three kinds of tonicity agents have a molecular weight of larger than 200, a dimensional change of the contact lens cannot be sufficiently controlled, and adverse effects are caused on the properties of the disinfecting solution such as the disinfecting effect and compatibility with respect to the contact lens since the tonicity agents are used in excessively large amounts for adjusting tonicity of the disinfecting solution.

Various known low-molecular-weight compounds (except Na salts or other salts of a carboxylic acid) having at least one carboxyl group (—COOH) and the molecular weight of not larger than 200 are used as the component (A), i.e. the acidic tonicity agent, among the above-indicated three kinds of tonicity agents. Examples of the acidic tonicity agent include a glycolic acid, a tartaric acid, a malic acid, a fumaric acid, a maleic acid, an aspartic acid, a glutamic acid and a citric acid. In the present invention, at least one of the above-indicated acidic tonicity agents is preferably selected and used as the component (A).

The component (B), i.e. the basic tonicity agent is adequately selected from various known low-molecular-weight compounds having the amino group (—$NH_2$) and the molecular weight of not larger than 200, such as ammonia, monoethanolamine, diethanolamine, triethanolamine, 2-amino-2-methyl-1-propanol (AMP), 2-amino-2-methyl-1,3-propanediol (AMPD) and trometamol. In the present invention, at least one of the above-indicated basic tonicity agents is advantageously selected and used as the component (B).

The component (C), i.e. at least one of the nonionic tonicity agent and the amphoteric tonicity agent is adequately selected from known compounds having the molecular weight of not larger than 200. Examples of the nonionic tonicity agent preferably used in the present invention include propylene glycol, glycerol, 1,3-propanediol, butylene glycol, erythritol, sorbitol, mannitol and xylitol. Examples of the amphoteric tonicity agent preferably used in the present invention include glycine, trimethylglycine, taurine and serine. In the present invention, at least one of the above-indicated nonionic tonicity agents and amphoteric tonicity agents is selected and used as the component (C), but use of a combination of the nonionic tonicity agents and the amphoteric tonicity agents is particularly effective. The nonionic tonicity agents and the amphoteric tonicity agents are also used for adjusting the osmotic pressure and electric conductivity of the disinfecting solution to be obtained as an end product, since addition of those tonicity agents cause only a small increase of the electric conductivity.

Concentrations of the above-described three kinds of low-molecular-weight tonicity agents in the disinfecting solution are required to be adjusted such that a total amount of the component (A) is 0.1-1.0% by weight, and a total amount of the component (B) is 0.10-1.25% by weight, while a total amount of the component (C) is 0.1-2.0% by weight. Where excessively small amounts of the components (A), (B) and (C) are contained in the disinfecting solution, it is difficult to sufficiently achieve operational and physical advantages owing to addition of those components. On the other hand, where the components (A), (B) and (C) are contained in the disinfecting solution in amounts exceeding the respective upper limits indicated above, the properties of the disinfecting solution, such as the disinfecting effect and compatibility with respect to the contact lens are deteriorated, so that it is difficult to sufficiently achieve the objects of the present invention.

In the present invention, within the above-indicated ranges of contents of the components (A), (B) and (C), the contents of the components (A) and (B) are required to be adjusted such that a ratio $\alpha/\beta$ of a molar concentration $\alpha$ of the component (A) to a molar concentration $\beta$ of the component (B) is not larger than 1.2, since the ratio $\alpha/\beta$ larger than 1.2 gives rise to problems such as insufficiency of the disinfecting effect.

The disinfecting solution for the nonionic soft contact lens according to the present invention is prepared by dissolving the predetermined amounts of the above-described three kinds of tonicity agents together with polylysine in an aqueous medium mainly composed of water, whereby the disinfecting solution having the osmotic pressure of 250-330 mOsm/kg is obtained, to prevent occurrence of ocular irritation at the time of wearing of the nonionic soft contact lens subjected to a disinfecting treatment using the disinfecting solution.

Further, the electric conductivity of the disinfecting solution for the nonionic soft contact lens according to the present invention is required to be adjusted within a range of 130-750 mS/m. The electric conductivity of the disinfecting solution can be adjusted within this range by preparing the disinfecting solution so as to contain various combinations of the above-described three kinds of tonicity agents used in the respective amounts described above, basically without using other tonicity agents having high degrees of ionic strength, such as sodium chloride. The electric conductivity lower than 130 mS/m causes deterioration of compatibility of the disinfecting solution with respect to the contact lens, giving rise to a risk of problems such as a large dimensional change of the nonionic soft contact lens immersed in the disinfecting solution. On the other hand, the electric conductivity higher than 750 mS/m gives rise to problems such as deterioration of the disinfecting effect of the disinfecting solution.

The pH of the disinfecting solution for the nonionic soft contact lens according to the present invention is adjusted within a range of 6.5 to 8.0, in order to make the disinfecting solution advantageously exhibit the disinfecting effect, and prevent occurrence of the ocular irritation at the time of wearing of the nonionic soft contact lens subjected to the disinfecting treatment using the disinfecting solution. In order to adjust the pH within the above-described range, acids such as HCl and alkalines such as NaOH are adequately added to the disinfecting solution, as necessary, as in the case of the conventional disinfecting solution.

In the disinfecting solution for the nonionic soft contact lens according to the present invention, which solution contains the predetermined amounts of the above-described three kinds of tonicity agents together with polylysine, the disinfecting effect of polylysine which is liable to be affected by additives is not so much hindered, and compatibility of the disinfecting solution with respect to the contact lens is advantageously improved. In the disinfecting solution according to the present invention, various known disinfectants can be used in combination with polylysine. Namely, where the known disinfectant is used as a second disinfectant, in addition to polylysine used as the first disinfectant, the disinfecting effect of the disinfecting solution can be further improved, while the second disinfectant is effectively prevented from adsorbing to and accumulating on the contact lens. Among the known disinfectants, those having at least two repeating units of a biguanide group or a quaternary ammonium group in their main chains are advantageously used as the second disinfectant in the present invention. It is surprising that in the disinfecting solution composed according to the present invention so as to contain the three kinds of tonicity agents in a well-balanced manner, and so as to have the electric conductivity adjusted within the adequate range, adsorption and accumulation of the second disinfectant on the contact lens can be efficiently reduced or prevented, while the disinfecting solution maintains good compatibility with respect to the contact lens.

The disinfectants which have at least two repeating units of the biguanide group or the quaternary ammonium group in their main chains and which are suitably used as the second disinfectant are well known in the art. Examples of the second disinfectant include polyhexamethylene biguanide (PHMB) and alexidine, and biguanide polymers and quaternary ammonium salt germicides which are disclosed in Japanese Patent No. 3894945. Among them, PHMB, alexidine and polyquaterniums such as polyquaternium-1 and polyquaternium-6 are suitably used in the present invention. It was revealed that even where PHMB, alexidine and the polyquaterniums, which have relatively strong positive charges in the aqueous solution are used as the second disinfectant, accumulation of those disinfectants on the contact lens can be effectively reduced or prevented according to the present invention.

An amount of the second disinfectant used in combination with polylysine (the first disinfectant) to improve the disinfecting effect is adequately determined depending on the improvement to be achieved by the combination of the two kinds of disinfectants. The second disinfectant is generally contained in the disinfecting solution at a concentration of not lower than 0.1 ppm, and preferably not lower than 0.5 ppm, in order for the disinfecting solution to sufficiently exhibit the disinfecting effect improved owing to the use of the second disinfectant. The second disinfectant is generally contained in the disinfecting solution at a concentration of not higher than 50 ppm, and preferably not higher than 20 ppm, since an extremely high concentration of the second disinfectant results in an increased amount of the second disinfectant adsorbing to the contact lens.

Further, various known additives contained in the conventional contact lens solution may be selected and added, as necessary, to the disinfecting solution for the nonionic soft contact lens according to the present invention, which solution contains the above-described components. Examples of the additives include surfactants, chelating agents, thickening agents and protein-removing agents. Any one of the known additives may be used in the present invention, as long as the additive has a high degree of safety with respect to the living body, and does not affect the shape and physical properties of the nonionic soft contact lens. The additives are advantageously contained in the disinfecting solution in amounts that do not impede the operational and physical advantages of the present invention.

In order for the disinfecting solution for the nonionic soft contact lens according to the present invention to advantageously exhibit an effect (a cleaning effect) of removing stains such as eye mucus from the contact lens, cleaning agents in the form of the surfactants are desirably added to the disinfecting solution. Specific examples of the surfactants include polyglycerol fatty acid esters, polyoxyethylene alkyl ethers, polyoxyethylene-polyoxypropylene block copolymers, polyoxyethylene-polyoxypropylene ethylene diamines, polyoxyethylene sorbitan fatty acid esters, polyoxyethylene alkyl phenyl ether formaldehyde condensates, polyoxyethylene hydrogenated castor oils, polyoxyethylene alkyl phenyl ethers, polyoxyethylene glycerine fatty acid esters, polyoxyethylene sorbitol fatty acid esters, polyoxyethylene castor oils, polyoxyethylene sterols, polyoxyethylene hydrogenated sterols, polyoxyethylene fatty acid esters, polyoxyethylene-polyoxypropylene alkyl ethers, polyoxyethylene lanolin alcohols, polyoxyethylene alkylamines, polyoxyethylene alkylamides, polyoxyethylene alkylether phosphates and polysorbates. Any one or any combination of the above-indicated surfactants may be used.

The surfactants are generally used in an amount of about 0.001-5% by weight, preferably about 0.005-2% by weight, and more preferably about 0.01-1% by weight. Where the surfactants are used in an extremely small amount, the cleaning effect cannot be sufficiently exhibited. On the other hand, where the surfactants are used in an extremely large amount, a further improvement of the cleaning effect cannot be expected, and the ocular irritation may be caused due to the extremely large amount of the surfactants.

In order to prevent ions of metals such as calcium in the tear fluid from adsorbing to the nonionic soft contact lens, the chelating agents are desirably added to the disinfecting solution. Specific examples of the chelating agents include ethylenediamine tetraacetic acid (EDTA) and salts thereof, such as disodium ethylenediamine tetraacetate (EDTA.2Na) and trisodium ethylenediamine tetraacetate (EDTA.3Na). The chelating agents are generally used in an amount of about 0.01-0.50% by weight.

Examples of the thickening agents used as necessary include: various kinds of gums such as heteropolysaccharides; synthetic organic polymers such as polyvinyl alcohol, poly-N-vinylpyrolidone, polyethylene glycol, polypropylene glycol and polyacrylamide; cellulose derivatives such as hydroxyethyl cellulose and hydroxypropyl methylcellulose; and starch derivatives.

No special method is required to prepare the disinfecting solution for the nonionic soft contact lens according to the present invention, which solution contains the above-described components. The disinfecting solution can be easily obtained by adding the components to the aqueous medium such as a purified water and a distilled water, so that the components are dissolved in the aqueous medium, as in the preparation of the conventional contact lens solution.

The thus obtained disinfecting solution for the nonionic soft contact lens according to the present invention may be suitably used as a disinfecting and cleaning solution for the nonionic soft contact lens, a disinfecting and preserving solution for the nonionic soft contact lens, and a disinfecting, cleaning and preserving solution for the nonionic soft contact lens, as well as the disinfecting or sterilizing solution for the nonionic soft contact lens, to perform the conventional treatments of the nonionic soft contact lens.

The type of the nonionic soft contact lens to be treated with the disinfecting solution for the nonionic soft contact lens according to the present invention is not particularly limited, as long as the nonionic soft contact lens belongs to either of Groups I and II of FDA classification. For example, various known water-containing soft contact lenses composed of HEMA (hydroxyethyl methacrylate)-based polymers may be treated with the disinfecting solution according to the present invention. Further, the disinfecting solution according to the present invention can be applied to the soft contact lenses belonging to Group V. Specifically, the disinfecting solution can be applied to the soft contact lenses composed of silicone hydrogels, which contact lenses have become popular in recent years.

EXAMPLES

To clarify the present invention more specifically, some examples of experiments including embodiments of the present invention will be described, but it goes without saying that the present invention is by no means limited to the description of the illustrated examples. It is to be understood that the present invention may be embodied with various changes, modifications and improvements, which are not illustrated herein, and which may occur to those skilled in the art without departing from the spirit of the present invention.

Experiment 1

Initially, by using a soft contact lens solution obtained by adding polylysine as a disinfectant to sterilized purified water, three kinds of disinfecting solutions "a" to "c" having respective osmotic pressures and respective electric conductivities, which are indicated in Table 1 given below, were prepared by adding, to the above-described soft contact lens solution, NaCl as a tonicity agent having a high degree of ionic strength, propylene glycol (PG) as a nonionic tonicity agent, and a boric acid as an auxiliary disinfecting component, which were used in respective amounts indicated in Table 1. The pH of each disinfecting solution was adjusted to about 7.4, by adding an adequate amount of a pH adjusting agent (HCl or NaOH) to the disinfecting solution, as necessary.

Then, each of the thus obtained three kinds of disinfecting solutions "a" to "c" was subjected to disinfecting effect tests with respect to fungi: *Candida albicans* and *Acanthamoeba*, a lens compatibility test and a cytotoxicity test, as described below. Results of the tests are indicated in Table 1.

—Disinfecting Effect Tests—

Disinfecting Effect with Respect to *Candida albicans*

9.9 mL of the disinfecting solution to be evaluated was accommodated in a test tube, 0.1 mL of a bacterial liquid containing $10^7$-$10^8$ cfu/mL of *Candida albicans* (*Candida albicans* IFO 1594) was added thereto, and the disinfecting solution and the bacterial liquid were stirred, to finally obtain a bacterial suspension containing $10^5$-$10^6$ cfu/mL of the bacteria. After the thus obtained bacterial suspension was left at 23° C. for one hour, 1 mL of the suspension was taken out of the test tube, as a sample. The sample was subjected to 10-fold serial dilution by a method of mixing the sample with 9 mL of a neutralizing liquid (a LP-diluent-added ¼ Ringer's solution available from NIHON PHARMACEUTICAL CO., LTD., JAPAN). Then, a viable cell count of the sample subjected to the 10-fold serial dilution was measured by a plate dilution method using 20 mL of glucose-peptone agar medium. From the measured viable cell count, the viable cell count per mL of the above-mentioned sample was calculated, and a logarithmic reduction (log reduction) of the bacteria was determined according to the following equation:

Log reduction=log (the viable cell count per mL of the bacterial suspension immediately after preparation)−log (the viable cell count per mL of the bacterial suspension left at 23° C. for one hour)

Sterilizing efficacy (the disinfecting effect) of the disinfecting solution was evaluated from the value of the thus obtained logarithmic reduction (log reduction) of the bacteria, according to the criteria given below.

Excellent: log reduction is not smaller than 3
Good: log reduction is not smaller than 1 and smaller than 3
Poor: log reduction is smaller than 1

Disinfecting Effect with Respect to *Acanthamoeba*

A pre-cultured vegetative hypha of *Acanthamoeba* (*Acanthamoeba castellanii* ATCC50370) was collected from a flask, and a suspension of $5 \times 10^5$ cells/mL was prepared using a ¼ Ringer's solution. On the other hand, 5 mL of the disinfecting solution to be evaluated was accommodated in a test tube, 50 μL of the above-mentioned *Acanthamoeba* suspension was added thereto, and the disinfecting solution and the *Acanthamoeba* suspension were stirred, to finally obtain a diluted suspension containing $5 \times 10^3$ cells/mL of the amoebas.

After the diluted suspension was left at 22° C. for four hours, 20 μL of the diluted suspension was collected, and subjected to the 10-fold serial dilution by a method of mixing the diluted suspension with 180 μL of a neutralizing liquid (a LP-diluent-added ¼ Ringer's solution). 50 μL of a suspension of *Escherichia coli* adjusted to $1 \times 10^8$ cfu was added to the diluted suspension subjected to the 10-fold serial dilution, followed by cultivation for 14 days. Then, the number of viable amoebas was measured from wells in which amoeba multiplication was observed, and the number of the viable amoebas per mL of the above-mentioned diluted suspension was calculated from the measured number of the viable amoebas. The log reduction value was calculated according to the equation given below, and evaluated according to the criteria given below.

Log reduction=log (the number of the viable amoebas per mL of the diluted suspension immediately after preparation)−log (the number of the viable amoebas per mL of the diluted suspension left at 22° C. for four hours)

Excellent: log reduction is not smaller than 3
Good: log reduction is not smaller than 1 and smaller than 3
Poor: log reduction is smaller than 1

—Lens Compatibility Test—

A commercially available nonionic soft contact lens [Meniconsoft MA (trade name) available from Menicon Co., Ltd., JAPAN] as purchased was taken out of a solution (a preserving solution for distribution) contained in a wrapping package, and immersed in an ISO isotonic sodium chloride solution kept at 25° C., for conditioning. Then, while the soft contact lens was immersed in the ISO isotonic sodium chloride solution, the initial size (diameter: $D_0$) of the contact lens was measured by using a projector (manufactured by Nikon Corporation, JAPAN; model number: V12A) at 20-fold magnification.

The soft contact lens was taken out of the ISO isotonic sodium chloride solution and immersed and left in 4 mL of the disinfecting solution to be evaluated for not shorter than four hours. Then, the soft contact lens was taken out of the disinfecting solution and immersed and left in another 4 mL of the disinfecting solution for not shorter than four hours. After the above-described operation of immersing the soft contact lens in the disinfecting solution was repeated by a total of 30 cycles, the size (diameter: $D_1$) of the soft contact lens was measured as described above. An amount of change in the size of the soft contact lens was calculated by subtracting the size ($D_0$) measured before the immersing operation from the size ($D_1$) measured after the immersing operation. Compatibility of the disinfecting solution with respect to the soft contact lens was evaluated from the calculated amount of the change in the size of the soft contact lens, according to the following criteria:

Good: the amount of change in the size is not larger than ±0.2 mm
Poor: the amount of change in the size is larger than ±0.2 mm —Cytotoxicity Test of Treated Contact Lens—

The commercially available nonionic soft contact lens (Meniconsoft MA) which was subjected, in the above-described lens compatibility test, to 30 cycles of the operation of immersing the soft contact lens in the disinfecting solution to be evaluated, was provided as a treated contact lens.

Initially, about 100 cells of V79 cell (Chinese hamster lung-derived fibroblast) were disseminated in a cell culture liquid (5 vol % bovine fetal serum-added MEM medium) accommodated in each well, and left for four hours. Then, the treated contact lens described above was put in each well, and cultivation was conducted for one week. Then, the number of cell colonies formed in the culture liquid was counted, and the colony formation percentage was calculated according to the equation given below. For the purpose of comparison, there were counted the numbers of cell colonies formed in wells accommodating a culture liquid in which the treated contact lens was not immersed and which was cultivated for one week.

Colony formation percentage (%)=(an average number of the cell colonies formed in the culture liquid in which the treated contact lens was immersed)/(an average number of the cell colonies formed in the culture liquid in which the treated contact lens was not immersed)×100

The cytotoxicity was evaluated from the above-described colony formation percentage, according to the following criteria:

Good: the colony formation percentage is not lower than 80%
Average: the colony formation percentage is not lower than 10% and lower than 80%
Poor: the colony formation percentage is lower than 10%

TABLE 1

| | | Disinfecting Solution "a" | Disinfecting Solution "b" | Disinfecting Solution "c" |
|---|---|---|---|---|
| Addition Amount (weight %) | ε-polylysine | 0.002 | 0.002 | 0.002 |
| | NaCl | — | 0.9 | 0.45 |
| | PG | 2 | — | — |
| | Boric Acid | — | — | 1 |
| | pH | 7.4 | 7.4 | 7.4 |
| | Osmotic Pressure (mOsm/kg) | 275 | 286 | 278 |
| | Electric Conductivity (mS/m) | 4 | 1535 | 887 |
| Disinfecting Effect | *Candida albicans* | Excellent | Poor | Good |
| | *Acanthamoeba* | Excellent | Poor | Good |
| Lens Compatibility | | Poor | Good | Poor |
| Cytotoxicity of Treated Contact Lens | | Good | Good | Poor |

As is apparent from the results indicated in Table 1, the disinfecting solution "a" containing polylysine and the nonionic tonicity agent (PG) used for the tonicity adjustment has a poor compatibility with respect to the contact lens, namely, suffered from swelling and a large dimensional change of the nonionic soft contact lens immersed in the disinfecting solution. On the other hand, the disinfecting solution "b"

containing polylysine and the tonicity agent (NaCl) having the high degree of ionic strength used for the tonicity adjustment suffered from considerable deterioration of the disinfecting effect of polylysine. The disinfecting solution "c" containing the boric acid used as the auxiliary disinfecting component together with NaCl used as the tonicity agent exhibited a disinfecting effect to some extent, but suffered from the dimensional change of the contact lens due to the boric acid used as the auxiliary disinfecting component, and a further problem of cytotoxicity due to the boric acid adsorbing to the contact lens and accumulated thereon.

Experiment 2

Various kinds of disinfecting solutions were prepared by adding, to sterilized purified water, predetermined components which were used in respective amounts shown Tables 2 and 3 given below, together with $\epsilon$-polylysine. The osmotic pressures of the disinfecting solutions were adjusted so as to be substantially equal to the physiological osmotic pressure, by further adding an adequate amount of the pH adjusting agent (HCl or NaOH) to the disinfecting solutions, as necessary. Each of the thus obtained various kinds of disinfecting solutions was measured of its osmotic pressure and electric conductivity. Further, the molar ratio (the molar concentration ratio) of the component (A) to the component (B) was calculated. Results of the measurements and calculation are indicated in Tables 2 and 3. Further, evaluations of the disinfecting effect and compatibility with respect to the contact lens (by performing 30 cycles of the immersing operation) were conducted as in the Experiment 1 described above. Results of the evaluations are indicated in Tables 2 and 3.

TABLE 2

| | | | Disinfecting Solutions | | | | | |
| --- | --- | --- | --- | --- | --- | --- | --- | --- |
| | | | 1 | 2 | 3 | 4 | 5 | 6 |
| Addition Amount (weight %) | First Disinfectant | $\epsilon$-polylysine | 0.02 | 0.02 | 0.02 | 0.02 | 0.02 | 0.02 |
| | Chelating Agent | EDTA · 2Na | 0.05 | — | 0.05 | 0.05 | — | 0.05 |
| | Acidic Tonicity Agent (A) | Glycolic Acid | 0.02 | — | 0.25 | 0.45 | 0.45 | — |
| | | Tartaric Acid | — | — | 0.10 | — | — | — |
| | | Succinic Acid | — | — | — | — | — | 0.40 |
| | | Glutamic Acid | — | 0.60 | — | — | — | — |
| | Basic Tonicity Agent (B) | AMPD | — | 0.73 | — | — | — | 0.65 |
| | | Trometamol | — | — | — | 0.77 | — | — |
| | | Monoethanolamine | — | — | — | — | 0.39 | — |
| | | Ammonia | 0.20 | — | 0.21 | — | — | — |
| | Amphoteric or Nonionic Tonicity Agent (C) | Glycine | 0.65 | — | 0.50 | 0.50 | 0.50 | 0.60 |
| | | Trimethylglycine | — | 0.60 | — | — | — | — |
| | | PG | 0.30 | — | 0.50 | 0.65 | 0.65 | 0.65 |
| | | Glycerol | — | 0.60 | — | — | — | 0.10 |
| | | Erythritol | 0.10 | — | — | — | — | — |
| | | Sorbitol | — | — | — | — | 0.10 | — |
| | Other Additives (D) | 2Na Hydrogen Phosphate | 0.10 | — | — | — | — | — |
| | pH | | Adjusted within a range of 7.4 ± 0.2 | | | | | |
| Osmotic Pressure (mOsm/kg) | | | 315 | 293 | 287 | 291 | 288 | 272 |
| Electric Conductivity (mS/m) | | | 142 | 468 | 732 | 334 | 329 | 418 |
| Component (A)/Component (B) (Molar Ratio) | | | 0.11 | 0.59 | 0.32 | 0.93 | 0.93 | 0.55 |
| Disinfecting Effect | | *Candida albicans* | Good | Good | Good | Good | Good | Good |
| | | *Acanthamoeba* | Good | Good | Good | Good | Good | Good |
| Lens Compatibility (30 cycles) | | | Good | Good | Good | Good | Good | Good |

| | | | Disinfecting Solutions | | | | |
| --- | --- | --- | --- | --- | --- | --- | --- |
| | | | 7 | 8 | 9 | 10 | 11 |
| Addition Amount (weight %) | First Disinfectant | $\epsilon$-polylysine | 0.02 | 0.02 | 0.02 | 0.02 | 0.02 |
| | Chelating Agent | EDTA · 2Na | 0.05 | 0.05 | 0.05 | 0.05 | 0.05 |
| | Acidic Tonicity Agent (A) | Glycolic Acid | 0.50 | 0.60 | 1.00 | 0.13 | 1.20 |
| | | Tartaric Acid | — | — | — | — | — |
| | | Succinic Acid | — | — | — | — | — |
| | | Glutamic Acid | — | — | — | — | — |
| | Basic Tonicity Agent (B) | AMPD | 1.20 | 1.30 | 1.60 | 0.21 | — |
| | | Trometamol | — | — | — | — | — |
| | | Monoethanolamine | — | — | — | — | — |
| | | Ammonia | — | — | — | — | — |
| | Amphoteric or Nonionic Tonicity Agent (C) | Glycine | — | — | — | 0.80 | — |
| | | Trimethylglycine | — | — | — | — | — |
| | | PG | 0.55 | 0.40 | — | 1.00 | — |
| | | Glycerol | — | — | — | — | — |
| | | Erythritol | — | — | — | — | — |
| | | Sorbitol | — | — | — | — | — |
| | Other Additives (D) | 2Na Hydrogen Phosphate | — | — | — | — | — |
| | pH | | Adjusted within a range of 7.4 ± 0.2 | | | | |

TABLE 2-continued

|  |  |  |  |  |  |
|---|---|---|---|---|---|
| Osmotic Pressure (mOsm/kg) | 287 | 280 | 276 | 277 | 307 |
| Electric Conductivity (mS/m) | 732 | 762 | 906 | 115.7 | 1068 |
| Component (A)/Component (B) (Molar Ratio) | 0.58 | 0.64 | 0.86 | 0.9 | — |
| Disinfecting Effect *Candida albicans* | Good | Poor | Poor | Good | Poor |
| *Acanthamoeba* | Good | Good | Poor | Good | Poor |
| Lens Compatibility (30 cycles) | Good | Good | Poor | Poor | Good |

TABLE 3

| | | | Disinfecting Solutions | | | | | |
|---|---|---|---|---|---|---|---|---|
| | | | 12 | 13 | 14 | 15 | 16 | 17 |
| Addition Amount (weight %) | First Disinfectant | ε-polylysine | 0.02 | 0.02 | 0.02 | 0.02 | 0.02 | 0.02 |
| | Chelating Agent | EDTA·2Na | 0.05 | 0.05 | 0.05 | 0.05 | 0.05 | 0.05 |
| | Acidic Tonicity Agent (A) | Glycolic Acid | — | 0.01 | — | — | 1.2 | — |
| | | Glutamic Acid | — | — | — | 2.10 | — | — |
| | Basic Tonicity Agent (B) | AMPD | 1.65 | 0.02 | — | 1.65 | — | 0.40 |
| | | Trometamol | — | — | — | — | — | — |
| | | Monoethanolamine | — | — | — | — | — | — |
| | | Ammonia | — | — | — | — | 0.21 | — |
| | Amphoteric or Nonionic Tonicity Agent (C) | Glycine | — | 2.10 | — | — | — | 0.60 |
| | | PG | — | — | 2.10 | — | — | 1.00 |
| | Other Additives (D) | Boric Acid | — | — | — | — | — | — |
| | | Na Pyrophosphate | — | — | — | — | — | — |
| | | 2Na Hydrogen Phosphate | — | — | — | — | — | — |
| | | Na Dihydrogen Phosphate | — | — | — | — | — | — |
| | | NaCl | — | — | — | — | — | — |
| | | Sodium Glutamate | — | — | — | — | — | — |
| pH | | | Adjusted within a range of 7.4 ± 0.2 | | | | | |
| Osmotic Pressure (mOsm/kg) | | | 282 | 281 | 293 | 299 | 305 | 287 |
| Electric Conductivity (mS/m) | | | 1070 | 49 | 37 | 540 | 739 | 237 |
| Component (A)/Component (B) (Molar Ratio) | | | — | 0.69 | — | 0.91 | 1.28 | — |
| Disinfecting Effect | *Candida albicans* | | Good | Good | Good | Poor | Poor | Good |
| | *Acanthamoeba* | | Good | Good | Good | Poor | Poor | Good |
| Lens Compatibility (30 cycles) | | | Poor | Poor | Poor | Poor | Good | Poor |

| | | | Disinfecting Solutions | | | | |
|---|---|---|---|---|---|---|---|
| | | | 18 | 19 | 20 | 21 | 22 |
| Addition Amount (weight %) | First Disinfectant | ε-polylysine | 0.02 | 0.02 | 0.02 | 0.02 | 0.02 |
| | Chelating Agent | EDTA·2Na | 0.05 | — | 0.05 | 0.05 | 0.05 |
| | Acidic Tonicity Agent (A) | Glycolic Acid | — | — | — | — | — |
| | | Glutamic Acid | — | — | — | — | — |
| | Basic Tonicity Agent (B) | AMPD | — | — | — | — | — |
| | | Trometamol | — | — | — | 0.30 | — |
| | | Monoethanolamine | 0.50 | — | — | — | — |
| | | Ammonia | — | — | — | — | — |
| | Amphoteric or Nonionic Tonicity Agent (C) | Glycine | — | — | — | 0.90 | — |
| | | PG | 1.00 | — | — | — | — |
| | Other Additives (D) | Boric Acid | — | — | — | — | 1.00 |
| | | Na Pyrophosphate | — | — | — | — | 0.50 |
| | | 2Na Hydrogen Phosphate | — | 3.30 | — | 0.52 | — |
| | | Na Dihydrogen Phosphate | — | 0.36 | — | 0.08 | — |
| | | NaCl | — | — | 0.90 | — | 0.25 |
| | | Sodium Glutamate | — | — | — | 0.70 | — |
| pH | | | Adjusted within a range of 7.4 ± 0.2 | | | | |
| Osmotic Pressure (mOsm/kg) | | | 291 | 264 | 287 | 280 | 291 |
| Electric Conductivity (mS/m) | | | 565 | 1333 | 1541 | 705.0 | 905 |
| Component (A)/Component (B) | | | — | — | — | 1.7 | — |

TABLE 3-continued

| (Molar Ratio) | | | | | | |
|---|---|---|---|---|---|---|
| Disinfecting Effect | *Candida albicans* | Good | Poor | Poor | Poor | Poor |
| | *Acanthamoeba* | Good | Poor | Poor | Poor | Poor |
| Lens Compatibility (30 cycles) | | Poor | Good | Good | Good | Poor |

As is apparent from the results indicated in Tables 2 and 3, the disinfecting solutions Nos. 1-7 according to the present invention contain the three kinds of low-molecular-weight tonicity agents consisting of the acidic tonicity agent (A), the basic tonicity agent (B) and the amphoteric and/or nonionic tonicity agent (C), in a well-balanced manner, together with polylysine, so that the disinfecting solutions Nos. 1-7 can exhibit an excellent disinfecting effect of polylysine with respect to the fungi and *Acanthamoeba*, and excellent compatibility with respect to the contact lens, causing only a small dimensional change of the contact lens.

On the other hand, the disinfecting solutions Nos. 8-22 have at least one problem in terms of their properties such as the disinfecting effect and compatibility with respect to the contact lens. The disinfecting solutions Nos. 9, 11, 12 and 14-18 contain only one or two of the three kinds of the components A, B and C. The disinfecting solution No. 13 contains excessively small amounts of the components A, B and C. The disinfecting solution No. 8 contains excessively large amounts of the components A, B and C. The disinfecting solution No. 10 has an excessively low electric conductivity. The disinfecting solutions Nos. 19-21 were prepared by using inorganic tonicity agents and tonicity agents in the form of salts, for adjusting tonicity. The disinfecting solution No. 22 contains an auxiliary disinfectant.

Experiment 3

Various kinds of disinfecting solutions having respective osmotic pressures and respective electric conductivities, which are indicated in Table 4 given below, were prepared by adding predetermined amounts of various components indicated in Table 4 to soft contact lens solutions obtained by dissolving, in sterilized purified water, PHMB (COSMOCIL CQ, available from NIKKO CHEMICALS CO., LTD., JAPAN) or polyquaternium-6 (available from Katayama Nalco Inc., JAPAN; trade name: Merquat 100; nitrogen content of 11% by weight) used as a second disinfectant, together with ε-polylysine used as a first disinfectant. The pH of each disinfecting solution was adjusted by using HCl or NaOH, as necessary. As for the thus obtained various kinds of disinfecting solutions, amounts of the respective disinfectants adsorbing to the soft contact lens were measured as described below. Results of the measurement are indicated in Table 4.

—Evaluation of Amount of Polylysine Adsorbing to Contact Lens—

As commercially available soft contact lenses as purchased, Meniconsoft MA (trade name; available from Menicon Co., Ltd.) which is a nonionic GI lens, and O₂ Optics (trade name; available from Ciba Vision K.K., JAPAN) which is a nonionic silicone hydrogel lens were provided. Each of the above-indicated soft contact lenses was taken out of a solution (a preserving solution for distribution) contained in a wrapping package, and immersed in an ISO isotonic sodium chloride solution for conditioning. Then, each soft contact lens was immersed in 4 mL of the disinfecting solution to be evaluated, for three days. The concentration of polylysine in the disinfecting solution was measured before and after the contact lens was immersed in the disinfecting solution, according to a determination method of ε-polylysine in the food additive standards. The amount of polylysine adsorbing to the contact lens was calculated according to the following equation:

Amount (%) of polylysine adsorbing to the contact lens=[1-{the concentration (w/v %) of polylysine in the disinfecting solution after immersing the contact lens}/{the concentration (w/v %) of polylysine in the disinfecting solution before immersing the contact lens}]×100

—Evaluation of Amount of Second Disinfectant (PHMB) Adsorbing to Contact Lens Surface—

One piece of O₂ Optics (trade name; available from Ciba Vision K.K.) described above was provided as the soft contact lens, and immersed in 4 mL of the disinfecting solution to be evaluated, for not shorter than one night. Then, the soft contact lens was immersed in 7 mL of an aqueous solution containing Eosin Y (sodium tetrabromofluorescein) (about 0.2 mg of Eosin Y and about 5.6 mg of sodium acetate were contained per mL of the aqueous solution), for about 30 seconds. Thereafter, the soft contact lens was taken out of the aqueous solution and immersed in 7 mL of ethanol for about 30 seconds, to remove excessive Eosin Y adsorbing to the lens. Then, the soft contact lens was immersed in an isotonic sodium chloride solution listed in the Japanese Pharmacopoeia, for conditioning. After conditioning, the soft contact lens was measured of its absorbing spectrum under the following conditions.

Conditions of Analysis
Wavelength Range: 450-600 nm
Slit Width: 12 nm
Measurement Mode: ABS.

Absorbance (indicating the amount of the disinfectant adsorbing to the contact lens) of the contact lens immersed in each of the disinfecting solutions Nos. 24-28, at the maximal absorption wavelength, is indicated as a percentage value with respect to an absorbance of the contact lens immersed in the disinfecting solution No. 23, at the maximal absorption wavelength, provided that the absorbance of the contact lens immersed in the disinfecting solution No. 23 at the maximal absorption wavelength is 100%.

—Evaluation of Amount of Second Disinfectant (Polyquaternium-6) Adsorbing to Contact Lens Surface—

One piece of O₂ Optics (trade name; available from Ciba Vision K.K.) described above was immersed in 4 mL of the disinfecting solution to be evaluated, for not shorter than one night, and then taken out of the disinfecting solution. The concentration of polyquaternium-6 in the disinfecting solution was measured before and after the contact lens was immersed in the disinfecting solution, according to the document indicated below. Amounts of polyquaternium-6 adsorbing to the respective contact lenses immersed in the respective disinfecting solutions Nos. 30 and 31 were compared with an amount of polyquaternium-6 adsorbing to the contact lens immersed in the disinfecting solution No. 29, and indicated as percentage values, provided that the amount of polyquaternium-6 adsorbing to the contact lens immersed in the disinfecting solution No. 29 is 100%

Referenced Document: "J. Assoc. of Anal. Chem." 1987, November-December; 70(6); 979-980 Colorimetric determination of a polymeric quaternary ammonium antimicrobial preservative in an ophthalmic solution.

TABLE 4

| | | | Disinfecting Solutions | | | | |
|---|---|---|---|---|---|---|---|
| | | | 23 | 24 | 25 | 26 | 27 |
| Addition Amount (weight %) | First Disinfectant | ε-polylysine | 0.02 | 0.02 | 0.02 | 0.02 | 0.02 |
| | Second Disinfectant | PHMB | 0.0001 | 0.0001 | 0.0001 | 0.0001 | 0.0001 |
| | | Polyquaternium-6 | — | — | — | — | — |
| | Acidic Tonicity Agent (A) | Glycolic Acid | — | 0.50 | — | — | — |
| | | Tartaric Acid | — | — | 0.50 | — | — |
| | | Aspartic Acid | — | — | — | 1.00 | — |
| | | Citric Acid | — | — | — | — | 0.50 |
| | Basic Tonicity Agent (B) | AMPD | — | 0.73 | 0.71 | 0.75 | — |
| | | Monoethanolamine | — | — | — | — | 0.50 |
| | Amphoteric or Nonionic Tonicity Agent (C) | PG | 1.40 | 0.65 | 0.90 | 0.65 | 0.50 |
| | | Glycine | 0.60 | 0.50 | 0.50 | 0.50 | 0.50 |
| | Other Additives (D) | Anhydrous Na Pyrophosphate | — | — | — | — | — |
| pH | | | \multicolumn{5}{c}{Adjusted within a range of 7.4 ± 0.05} | | | | |
| Osmotic Pressure (mOsm/kg) | | | 275 | 283 | 279 | 306 | 288 |
| Electric Conductivity (mS/m) | | | 38 | 442 | 465 | 542 | 483 |
| Component (A)/Component (B) (Molar Ratio) | | | — | 0.95 | 0.49 | 1.05 | 0.32 |
| Amount of Polylysine Adsorbing to Contact Lens | Meniconsoft MA | | 60% | 28% | 13% | 21% | 4% |
| | $O_2$ Optics | | 3% | less than detection limit | 2% | less than detection limit | 3% |
| Amount of Second Disinfectant Adsorbing to Contact Lens | $O_2$ Optics | | 100% | 34% | 28% | 36 | 17% |

| | | | Disinfecting Solutions | | | |
|---|---|---|---|---|---|---|
| | | | 28 | 29 | 30 | 31 |
| Addition Amount (weight %) | First Disinfectant | ε-polylysine | 0.02 | 0.02 | 0.02 | 0.02 |
| | Second Disinfectant | PHMB | 0.0001 | — | — | — |
| | | Polyquaternium-6 | — | 0.005 | 0.005 | 0.005 |
| | Acidic Tonicity Agent (A) | Glycolic Acid | — | — | 0.50 | — |
| | | Tartaric Acid | — | — | — | — |
| | | Aspartic Acid | — | — | — | — |
| | | Citric Acid | — | — | — | 0.50 |
| | Basic Tonicity Agent (B) | AMPD | — | — | 0.73 | — |
| | | Monoethanolamine | — | — | — | 0.50 |
| | Amphoteric or Nonionic Tonicity Agent (C) | PG | 0.90 | 1.40 | 0.65 | 0.50 |
| | | Glycine | 0.50 | 0.60 | 0.50 | 0.50 |
| | Other Additives (D) | Anhydrous Na Pyrophosphate | 0.50 | — | — | — |
| pH | | | \multicolumn{4}{c}{Adjusted within a range of 7.4 ± 0.05} | | | |
| Osmotic Pressure (mOsm/kg) | | | 291 | 274 | 283 | 281 |
| Electric Conductivity (mS/m) | | | 475 | 40 | 445 | 492 |
| Component (A)/Component (B) (Molar Ratio) | | | — | — | 0.95 | 0.32 |
| Amount of Polylysine Adsorbing to Contact Lens | Meniconsoft MA | | 2% | 65% | 33% | 3% |
| | $O_2$ Optics | | less than detection limit | less than detection limit | less than detection limit | less than detection limit |
| Amount of Second Disinfectant Adsorbing to Contact Lens | $O_2$ Optics | | 79% | 100% | less than detection limit | less than detection limit |

As is apparent from the results indicated in Table 4, the amount of polylysine as the first disinfectant adsorbing to the contact lens and the amounts of PHMB and polyquaternium-6 as the second disinfectant adsorbing to the contact lens are small in the disinfecting solutions Nos. 24-27, 30 and 31 prepared according to the present invention so as to contain the acidic tonicity agent (A), the basic tonicity agent (B) and the amphoteric or nonionic tonicity agent (C), in a well-balanced manner. Accordingly, it can be understood that a problem of occurrence of eye disorders due to accumulated disinfectants can be advantageously reduced or prevented in the disinfecting solutions Nos. 24-27, 30 and 31.

On the other hand, where the osmotic pressure of the disinfecting solution is adjusted by using only the tonicity agent (C), rather than the combination of the three kinds of tonicity agents, as in the case of the disinfecting solutions Nos. 23, 28 and 29, considerable amounts of the first disinfectant (polylysine) and the second disinfectant (PHMB and polyquaternium-6) adsorb to the contact lens, giving rise to an inherent risk of occurrence of the eye disorders due to the disinfectants adsorbing to and accumulated on the contact lens.

Experiment 4

Various kinds of disinfecting solutions having respective compositions indicated in Table 5 given below were prepared as in the Experiment 3. The thus obtained disinfecting solutions were subjected to a disinfecting effect test as described below. Results of the test are indicated in Table 5.

—Disinfecting Effect Test—

A commercially available soft contact lens: Meniconsoft MA (trade name; available from Menicon Co., Ltd.) as purchased was taken out of a solution (a preserving solution for distribution) contained in a wrapping package, and immersed in an ISO isotonic sodium chloride solution for conditioning. Then, the contact lens was immersed in 4 mL of the disinfecting solution to be evaluated, for three days.

After the contact lens was taken out of the disinfecting solution to be evaluated, 9.9 mL of the disinfecting solution was accommodated in a test tube, 0.1 mL of a bacterial liquid containing $10^7$-$10^8$ cfu/mL of *Candida albicans* (*Candida albicans* IFO 1594) or *Serratia marcescens* (*Serratia marcescens* ATCC13880) was added thereto, and the disinfecting solution and the bacterial liquid were stirred, to finally obtain a bacterial suspension containing $10^5$-$10^6$ cfu/mL of the bacteria. After the thus prepared bacterial suspension was left at 23° C. for one hour, 1 mL of the suspension was taken out of the test tube, as a sample. The sample was subjected to 10-fold serial dilution by a method of mixing the sample with 9 mL of a neutralizing liquid (a LP-diluent-added ¼ Ringer's solution available from NIHON PHARMACEUTICAL CO., LTD.). Then, a viable cell count of the sample subjected to the 10-fold serial dilution was measured by a plate dilution method using 20 mL of glucose-peptone agar medium. From this viable cell count, the viable cell count per mL of the above-mentioned sample was calculated, and a logarithmic reduction (log reduction) of the bacteria was determined according to the equation given below. The disinfecting effect with respect to each kind of bacteria was evaluated based on the log reduction of the bacteria.

Log reduction=log (the viable cell count per mL of the bacterial suspension immediately after preparation)−log (the viable cell count per mL of the bacterial suspension prepared by using the disinfecting solution in which the contact lens was immersed)

TABLE 5

| | | | Disinfecting Solutions | | | | |
|---|---|---|---|---|---|---|---|
| | | | 32 | 33 | 24 | 34 | 35 |
| Addition Amount (weight %) | First Disinfectant | ε-polylysine | 0.02 | 0.02 | 0.02 | 0.02 | 0.02 |
| | Second Disinfectant | PHMB | 0.0001 | 0.0001 | 0.0001 | 0.0001 | 0.0001 |
| | Acidic Tonicity Agent (A) | Glycolic Acid | — | — | 0.50 | — | — |
| | | Tartaric Acid | — | — | — | 0.25 | — |
| | | Aspartic Acid | — | — | — | — | 0.50 |
| | | Glutamic Acid | — | — | — | — | — |
| | Basic Tonicity Agent (B) | AMPD | — | — | 0.73 | 0.335 | 0.40 |
| | | Monoethanolamine | — | — | — | — | — |
| | | Ammonia | — | — | — | — | — |
| | Amphoteric or Nonionic Tonicity Agent (C) | PG | 0.65 | 0.90 | 0.65 | 1.20 | 1.00 |
| | | Glycine | 0.50 | 0.50 | 0.50 | 0.50 | 0.50 |
| | Other Additives (D) | NaCl | 0.40 | — | — | — | — |
| | | Na Pyrophosphate | — | 0.50 | — | — | — |
| pH | | | Adjusted within a range of 7.4 ± 0.2 | | | | |
| Osmotic Pressure (mOsm/kg) | | | 285 | 291 | 283 | 274 | 298 |
| Electric Conductivity (mS/m) | | | 42 | 475 | 442 | 189 | 286 |
| Component (A)/Component (B) (Molar Ratio) | | | — | — | 0.95 | 0.52 | 0.99 |
| Disinfecting Effect | S.Marcescens | | 4.1 | 2.4 | >4.4 | >4.4 | >4.4 |
| | C.albicans | | 0.1 | 0.3 | 2.1 | 1.0 | 2.3 |

TABLE 5-continued

| | | | Disinfecting Solutions | | | |
|---|---|---|---|---|---|---|
| | | | 26 | 36 | 37 | 38 |
| Addition Amount (weight %) | First Disinfectant | ε-olylysine | 0.02 | 0.02 | 0.02 | 0.02 |
| | Second Disinfectant | PHMB | 0.0001 | 0.0001 | 0.0001 | 0.0001 |
| | Acidic Tonicity Agent (A) | Glycolic Acid | — | — | 0.50 | 0.50 |
| | | Tartaric Acid | — | — | — | — |
| | | Aspartic Acid | 1.00 | — | — | — |
| | | Glutamic Acid | — | 1.00 | — | — |
| | Basic Tonicity Agent (B) | AMPD | 0.75 | 0.73 | — | — |
| | | Monoethanolamine | — | — | 0.42 | — |
| | | Ammonia | — | — | — | 0.145 |
| | Amphoteric or Nonionic Tonicity Agent (C) | PG | 0.65 | 0.65 | 0.65 | 0.65 |
| | | Glycine | 0.50 | 0.50 | 0.50 | 0.50 |
| | Other Additives (D) | NaCl | — | — | — | — |
| | | Na Pyrophosphate | — | — | — | — |
| pH | | | Adjusted within a range of 7.4 ± 0.2 | | | |
| Osmotic Pressure (mOsm/kg) | | | 306 | 293 | 286 | 290 |
| Electric Conductivity (mS/m) | | | 542 | 540 | 366 | 526 |
| Component (A)/Component (B) (Molar Ratio) | | | 1.05 | 0.98 | 0.96 | 0.77 |
| Disinfecting Effect | | S.Marcescens | >4.4 | >4.4 | >4.4 | >4.4 |
| | | C.albicans | 1.2 | 1.7 | 2.3 | 1.8 |

Unlike the disinfecting solutions Nos. 32 and 33 prepared by using only the amphoteric or nonionic tonicity agent (C) in combination with NaCl or Na pyrophosphate, the disinfecting solutions Nos. 24, 26 and 34-38 containing the three kinds of tonicity agents in a well-balanced manner according to the present invention have compositions configured so as to prevent adsorption of the first and second disinfectants to the soft contact lens, and so as not to hinder the effects of the disinfectants. Therefore, as is apparent from the results indicated in Table 5, the disinfecting solutions Nos. 24, 26 and 34-38 exhibit a remarkable disinfecting effect with respect to Serratia marcescens (S. marcescens), even after the contact lens was immersed in those disinfecting solutions. Also, it can be recognized that the disinfecting solutions Nos. 24, 26 and 34-38 maintain a relatively high degree of disinfecting effect with respect to Candida albicans (C. albicans), as compared with the disinfecting solutions Nos. 32 and 33.

The invention claimed is:

1. A disinfecting solution for a nonionic soft contact lens, which solution contains polylysine as a disinfectant,
   0.1-1.0% by weight of a component (A) which is an acidic tonicity agent having at least one carboxyl group and a molecular weight of not larger than 200, 0.10-1.25% by weight of a component (B) which is a basic tonicity agent having an amino group and a molecular weight of not larger than 200, and 0.1-2.0% by weight of a component (C) which is at least one of a nonionic tonicity agent which has a molecular weight of not larger than 200 or an amphoteric tonicity agent which has a molecular weight of not larger than 200, wherein a ratio (α/β) of a molar concentration (α) of said component (A) to a molar concentration (β) of said component (B) is not larger than 1.2; and
   the disinfecting solution has a pH of 6.5-8.0, an osmotic pressure of 250-330 mOsm/kg and an electric conductivity of 130-750 mS/m.

2. The disinfecting solution for the nonionic soft contact lens according to claim 1, further containing a second disinfectant having at least two repeating units of a biguanide group or a quaternary ammonium group in its main chain, in addition to a first disinfectant consisting of said polylysine.

3. The disinfecting solution for the nonionic soft contact lens according to claim 1, wherein the acidic tonicity agent is selected from a group consisting of a glycolic acid, a tartaric acid, a malic acid, a fumaric acid, a maleic acid, an aspartic acid, a glutamic acid and a citric acid.

4. The disinfecting solution for the nonionic soft contact lens according to claim 1, wherein the basic tonicity agent is selected from a group consisting of ammonia, monoethanolamine, diethanolamine, triethanolamine, 2-amino-2-methyl-1-propanol, 2-amino-2-methyl-1,3-propanediol, and trometamol.

5. The disinfecting solution for the nonionic soft contact lens according to claim 1, wherein the nonionic tonicity agent is present and is selected from a group consisting of propylene glycol, glycerol, 1,3-propanediol, butylene glycol, erythritol, sorbitol, mannitol and xylitol.

6. The disinfecting solution for the nonionic soft contact lens according to claim 1, wherein the amphoteric tonicity agent is present and is selected from a group consisting of glycine, trimethylglycine, taurine and serine.

7. The disinfecting solution for the nonionic soft contact lens according to claim 1, wherein said polylysine is ε-polylysine.

8. The disinfecting solution for the nonionic soft contact lens according to claim 2, wherein said second disinfectant is selected from a group consisting of polyhexamethylene biguanide, alexidine, polyquaternium-1 and polyquaternium-6.

9. The disinfecting solution for the nonionic soft contact lens according to claim 1, wherein said ratio (α/β) is not larger than 1.0.

10. The disinfecting solution for the nonionic soft contact lens according to claim 1, wherein a concentration of said polylysine is 1-1000 ppm.

11. The disinfecting solution for the nonionic soft contact lens according to claim 1, wherein a concentration of said polylysine is 10-500 ppm.

12. The disinfecting solution for the nonionic soft contact lens according to claim 2, wherein a concentration of said second disinfectant is 0.1-50 ppm.

13. The disinfecting solution for the nonionic soft contact lens according to claim 2, wherein a concentration of said second disinfectant is 0.5-20 ppm.

14. The disinfecting solution for the nonionic soft contact lens according to claim 1, wherein at least the nonionic tonicity agent is present.

15. The disinfecting solution for the nonionic soft contact lens according to claim 1, wherein at least the amphoteric tonicity agent is present.

16. The disinfecting solution for the nonionic soft contact lens according to claim 1, wherein the acidic tonicity agent is selected from a group consisting of a tartaric acid, a malic acid, a fumaric acid, a maleic acid, a glutamic acid and a citric acid.

17. The disinfecting solution for the nonionic soft contact lens according to claim 1, wherein the basic tonicity agent is selected from a group consisting of ammonia, monoethanolamine, diethanolamine, triethanolamine, 2-amino-2-methyl-1-propanol, and trometamol.

\* \* \* \* \*